US010391142B2

(12) United States Patent
Buser et al.

(10) Patent No.: US 10,391,142 B2
(45) Date of Patent: Aug. 27, 2019

(54) BIOMARKERS FOR PAINFUL INTERVERTEBRAL DISCS AND METHODS OF USE THEREOF

(71) Applicant: The Regents of the University of California, Oakland, CA (US)

(72) Inventors: Zorica Buser, San Francisco, CA (US); Jeffrey Charles Lotz, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/332,863

(22) Filed: Oct. 24, 2016

(65) Prior Publication Data

US 2017/0035844 A1    Feb. 9, 2017

Related U.S. Application Data

(63) Continuation of application No. 14/103,248, filed on Dec. 11, 2013, now abandoned, which is a continuation of application No. 12/994,281, filed as application No. PCT/US2009/003301 on May 29, 2009, now Pat. No. 8,609,334.

(60) Provisional application No. 61/056,967, filed on May 29, 2008.

(51) Int. Cl.

| G01N 33/68 | (2006.01) |
| A61K 31/565 | (2006.01) |
| A61K 38/17 | (2006.01) |
| A61K 31/7088 | (2006.01) |
| C12Q 1/6883 | (2018.01) |
| C12Q 1/6876 | (2018.01) |

(52) U.S. Cl.
CPC ........ *A61K 38/1709* (2013.01); *A61K 31/565* (2013.01); *A61K 31/7088* (2013.01); *C12Q 1/6876* (2013.01); *C12Q 1/6883* (2013.01); *G01N 33/6893* (2013.01); *C12Q 2600/158* (2013.01); *G01N 2800/2842* (2013.01)

(58) Field of Classification Search
None
See application file for complete search history.

(56) References Cited

U.S. PATENT DOCUMENTS

| 6,313,091 B1 | 11/2001 | Wisniewski et al. |
| 6,518,401 B1 | 2/2003 | Lee et al. |
| 2001/0006948 A1 | 7/2001 | Kang et al. |
| 2007/0015178 A1 | 1/2007 | Chubinskaya et al. |
| 2007/0065415 A1 | 3/2007 | Kleinsek et al. |
| 2007/0190149 A1 | 8/2007 | Zahos |
| 2008/0038233 A1 | 2/2008 | Freemont et al. |

FOREIGN PATENT DOCUMENTS

| WO | WO2007/101988 | 9/2007 |
| WO | WO2007/147140 | 12/2007 |

OTHER PUBLICATIONS

Miyahara et al., Human group II phospholipase A2 in normal and diseased intervertebral discs, (1996), Biochimica et Biophysica Acta 1316:183-190.*
"Rule 17, Exhibit 1" In: Department of Labor and Employment: "Low Back Pain Medical Treatment Guidelines", State of Colorado, 2007, pp. 1-65.
Bayliss et al., "Up-regulation and Differential Expression of the Hyaluronan-Binding Protein TSG-6 in Cartilage and Synovium in Rheumatoid Arthritis and Osteoarthritis", OsteoArthristic and Cartilage, 2001, 9:42-48.
Biyani, et al., "Low Back Pain: Pathophysiology and Management", Journal of American Academy of Orthopedic Surgeons, 2004, 12(2):106-115.
Diatchenko, et al., "Genetic Architecture of Human Pain Perception", Trends in Genetics, 2007, 23(12):605-613.
Freemont, et al., "Nerve Growth Factor Expression and Innervation of the Painful Intervertebral Disc", The Journal of Pathology, 2002, 197(3):286-292.
Garcia et al., "2-Methoxyestradiol Inhibits Prostate Tumor Development in Transgenic Adenocarcinoma of Mouse Prostate: Role of Tumor Necrosis Factor-A-Stimulated Gene 6", Clin Cancer Res, 2006, 12(3):980-988.
Gruber, et al., "Microarray Analysis of Laser Capture Microdissected-Anulus Cells from the Human Intervertebral Disc", Spine, 2007, 32(11):1181-1187.
Lee et al., "A Novel Secretory Tumor Necrosis Factor-inducible Protein (TSG-6) is a Member of the Family of Hyaluronate Binding Proteins, Closely Related to the Adhesion Receptor CD44", The Journal of Cell Biology, 1992, 116(2):545-557.
Lesley et al., "TSG-6 Modulates the Interaction between Hyaluronan and Cell Surface CD44*", The Journal of Biological Chemistry, 2004, 279(24):25745-25754.
Karppinen et al., "Radiologic phenotypes in lumbar MR imaging for a gene defect in the COL9A3 gene of Type IX collagen", Radiology, 2003, 227:143-148.
Maier et al., "TSG-6 Expression in Human Articular Chondrocytes", Arthritis & Rheumatism, 1996, 39(4):552-559.
Modic et al., "Lumbar Degenerative Disk Disease", Radiology, 2007, 245(1):43-61.
Mulleman, et al., "Pathophysiology of Disk-Related Low Back Pain and Sciatica II. Evidence Supporting Treatment with TNF-α Antagonists", Joint Bone Spine, 2006, 73(3):270-277.
Peng, at al., "Possible Pathogenesis of Painful Intervertebral Disc Degeneration", Spine, 2006, 31(5):560-566.
Roberts et al., "TNF Alpha-Stimulated Gene Product (TSG-6) and its Binding Protein, Ialphal, in the Human Intervertebral Disc: New Molecules for the Disc", European Spine Journal, 2005, 14(1):36-42.
Ulrich et al., "ISSLS Prize Winner: Repeated Disc Injury Causes Persistent Inflammation", Spine, 2007, 32(25):2812-2819.

* cited by examiner

Primary Examiner — John D Ulm
(74) *Attorney, Agent, or Firm* — Bozicevic Field & Francis, LLP; Paula A. Borden; Payal B. Sud

(57) ABSTRACT

The present disclosure provides methods of diagnosing painful intervertebral discs. The present disclosure also provides methods of treating a painful intervertebral disc.

18 Claims, 2 Drawing Sheets

Specification includes a Sequence Listing.

Figure 3A

```
  1 miiliylfll lwedtqgwgf kdgifhnsiw leraagvyhr earsgkyklt yaeakavcef
 61 egghlatykq leaarkigfh vcaagwmakg rvgypivkpg pncgfgktgi idygirlnrs
121 erwdaycynp hakecggvft dpkqifkspg fpneyednqi cywhirlkyg qrihlsfldf
181 dleddpgcla dyveiydsyd dvhgfvgryc gdelpddiis tgnvmtlkfl sdasvtaggf
241 qikyvamdpv skssqgknts ttstgnknfl agrfshl
```

Figure 3B

```
  1 atgatcatct taatttactt atttctcttg ctatgggaag acactcaagg atggggattc
 61 aaggatggaa tttttcataa ctccatatgg cttgaacgag cagccggtgt gtaccacaga
121 gaagcacggt ctggcaaata caagctcacc tacgcagaag ctaaggcggt gtgtgaattt
181 gaaggcggcc atctcgcaac ttacaagcag ctagaggcag ccagaaaaat tggatttcat
241 gtctgtgctg ctggatggat ggctaagggc agagttggat accccattgt gaagccaggg
301 cccaactgtg gatttggaaa aactggcatt attgattatg gaatccgtct caataggagt
361 gaaagatggg atgcctattg ctacaaccca cacgcaaagg agtgtggtgg cgtctttaca
421 gatccaaagc aaatttttaa atctccaggc ttcccaaatg agtacgaaga taaccaaatc
481 tgctactggc acattagact caagtatggt cagcgtattc acctgagttt tttagatttt
541 gaccttgaag atgacccagg ttgcttggct gattatgttg aaatatatga cagttacgat
601 gatgtccatg gctttgtggg aagatactgt ggagatgagc ttccagatga catcatcagt
661 acaggaaatg tcatgacctt gaagtttcta agtgatgctt cagtgacagc tggaggtttc
721 caaatcaaat atgttgcaat ggatcctgta tccaaatcca gtcaaggaaa aaatacaagt
781 actacttcta ctggaaataa aaacttttta gctggaagat ttagccactt ataa
```

BIOMARKERS FOR PAINFUL INTERVERTEBRAL DISCS AND METHODS OF USE THEREOF

CROSS-REFERENCE

This application claims the benefit of U.S. Provisional Patent Application No. 61/056,967, filed May 29, 2008, which application is incorporated herein by reference in its entirety.

STATEMENT REGARDING FEDERALLY SPONSORED RESEARCH

This invention was made with government support under grant no. AR052712 awarded by the National Institutes of Health. The government has certain rights in the invention.

BACKGROUND

The spinal intervertebral discs serve as the shock absorbers of the axial body and also allow for considerable flexibility and motion. Each disc is composed of a peripheral, ligament-like annulus fibrosus and a central nucleus pulposus (NP). The NP contains chondrocyte-like cells embedded in a matrix of proteoglycan and type II collagen that is highly hydrophilic and allows the tissue to swell to resist compressive forces. The NP environment is one of high pressure, low pH, and low oxygen tension.

Intervertebral disc degeneration is an age-related process in individuals both with and without back pain. A method for reliable and objective differentiation between painful and nonpainful degenerated discs remains a significant clinical challenge. For the majority of patients experiencing back pain, there is no clear diagnosis linking symptoms with pathological changes. Proper diagnosis is important for determination of an effective treatment.

There is a need in the art for methods of diagnosing painful intervertebral discs.

LITERATURE

Ulrich et al. (2007) *Spine* 32:2812; Maier et al. (1996) *Arthritis and Rheumatism* 39:552; Bayliss et al. (2001) *OsteoArthritis and Cartilage* 9:42; U.S. Pat. Nos. 6,313,091; 6,518,401.

SUMMARY OF THE INVENTION

The present disclosure provides methods of diagnosing painful intervertebral discs. The present disclosure also provides methods of treating a painful intervertebral disc.

BRIEF DESCRIPTION OF THE DRAWINGS

FIG. 3A presents an amino acid sequence (SEQ ID NO:1) of a tumor necrosis factor-alpha-induced protein 6 (TSG6) polypeptide. Amino acids in bold text indicate a hyaluronic acid-binding ("link") domain.

FIG. 3B presents a nucleotide sequence (SEQ ID NO:2) encoding a TGS6 polypeptide.

DEFINITIONS

Figure 1:
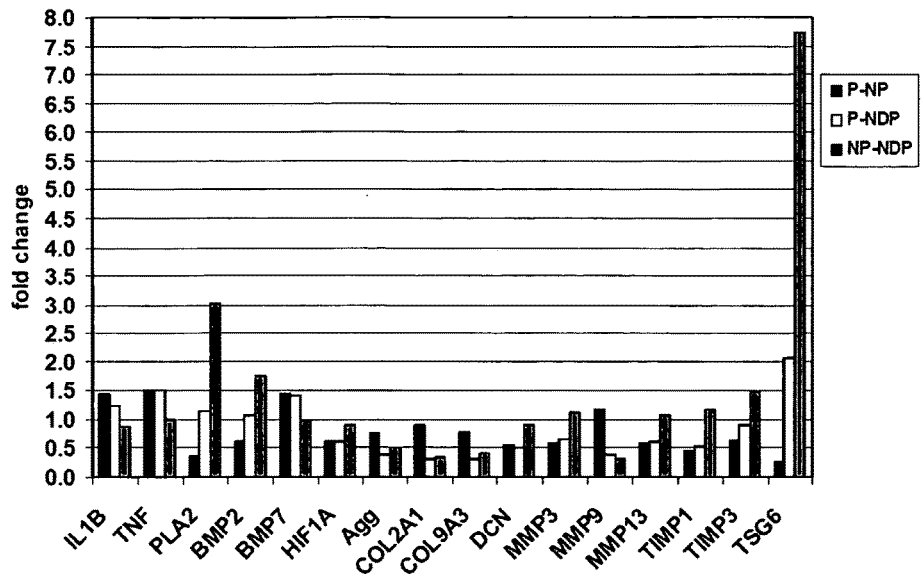
FIG. 1 depicts gene expression of nucleus pulposus samples (P=painful; NP=non painful degenerated; NDP=non painful non degenerated). For each gene, the first bar is P-NP; the second bar is P-NDP; and the third bar is NP-NDP.

The terms "gene product" and "expression product" are used interchangeably herein in reference to a gene, to refer to the RNA transcription products (transcripts) of the gene, including mRNA and the polypeptide translation products of such RNA transcripts, whether such product is modified post-translationally or not. The terms "gene product" and "expression product" are used interchangeably herein, in reference to an RNA, particularly an mRNA, to refer to the polypeptide translation products of such RNA, whether such product is modified post-translationally or not. A gene product can be, for example, an unspliced RNA, an mRNA, a splice variant mRNA, a polypeptide, a post-translationally modified polypeptide, a splice variant polypeptide, etc.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. "Polypeptide" includes polypeptides that comprise one or more sugar moieties, one or more lipid moieties, one or more phosphoryl groups, or other post-translational modifications.

The terms "subject," "individual," "host," and "patient" are used interchangeably herein to refer to a member or members of any mammalian species. Individuals thus include, without limitation, humans, non-human primates, canines, felines, ungulates (e.g., equine (e.g., horses), bovine (e.g., cows), swine (e.g., pig), camels, etc.), rodents (e.g., rats, mice), and other mammalian subjects. Non-human animal models, particularly mammals, e.g. a non-human primate, a murine (e.g., a mouse, a rat), lagomorpha, etc. may be used for experimental investigations.

"Treating" or "treatment" of a condition, disorder, or disease includes: (1) preventing at least one symptom of the condition, disorder, or disease, e.g., causing a clinical symptom to not significantly develop in a mammal that may be exposed to or predisposed to a disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammalian subject for the treatment of a condition, disorder, or disease, is sufficient, in combination with another agent, or alone in one or more doses, to effect such treatment for the condition, disorder, or disease. The "therapeutically effective amount" will vary depending on the compound, the condition, disorder, or disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a gene product" includes a plurality of such gene products and reference to "the TSG6 polypeptide" includes reference to one or more TSG6 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of diagnosing painful intervertebral discs. The methods generally involve assaying a level of one or more gene products in an intervertebral disc. Certain gene product(s) have been determined to provide an indication as to whether a given intervertebral disc is painful. Such gene products are referred to herein as "pain indicator gene products." The level of pain indicator gene product, compared to a normal range, indicates whether the intervertebral disc is painful. Diagnosis of a painful intervertebral disc can allow a medical professional to recommend a treatment. Thus, the present disclosure also provides methods of treating a painful intervertebral disc.

Diagnostic Methods

The present disclosure provides methods of diagnosing painful intervertebral discs. The methods generally involve assaying a level of a pain indicator gene product in an intervertebral disc tissue. A level of a pain indicator gene product indicates whether an intervertebral disc is painful.

Pain Indicator Genes

Certain gene products were identified, where expression levels of the gene products provide an indication as to whether a given intervertebral disc is painful. As noted above, these gene products are referred to herein as "pain indicator gene products"; and genes encoding the pain indicator gene products are referred to as "pain indicator genes."

An intervertebral disc is composed of a peripheral annulus fibrosus and a central nucleus pulposus (NP). An expression level of a pain indicator gene in the annulus fibrosus of an intervertebral disc can be assayed, e.g., an annulus fibrosus pain indicator gene product expression level can be assayed. An expression level of a pain indicator gene in the NP of an intervertebral disc can be assayed, e.g., an NP pain indicator gene product expression level can be assayed. Alternatively, an expression level of a pain indicator gene product in the annulus fibrosus and the NP can be assayed.

Pain indicator genes include: COL2A, COL9A3, AGC1, DCN, MMP3, MMP13, TIMP1, TIMP3, CD44, BMP2, HIF1, IL8, IL1R, PLA2, TSG6, MMP9, Col1A1, and Col3. Decreased expression levels of each of these genes correlates positively with a painful intervertebral disc. In other words, a decreased expression level of one or more of these genes in a tissue of an intervertebral disc indicates that the intervertebral disc is painful.

As noted above, pain indicator gene expression levels can be detected in the annulus fibrosus of an intervertebral disc. Pain indicator genes that can be detected in the annulus fibrosus include: PLA2, MMP9, TSG6, Col1A1, and Col3. Decreased expression levels of each of these genes correlates positively with a painful intervertebral disc. In other words, a decreased expression level of one or more of these genes in the annulus fibrosus of an intervertebral disc indicates that the intervertebral disc is painful.

Similarly, pain indicator gene expression levels can be detected in the NP of an intervertebral disc. Pain indicator genes that can be detected in the NP include: COL2A, COL9A3, AGC1, DCN, MMP3, MMP13, TIMP1, TIMP3, CD44, BMP2, HIF1, IL8, IL1R, PLA2, and TSG6. Decreased expression levels of each of these genes correlates positively with a painful intervertebral disc. In other words, a decreased expression level of one or more of these genes in the NP of an intervertebral disc indicates that the intervertebral disc is painful.

Pain indicator genes also include: BMP7, TNF-$\alpha$, IL1$\beta$, PGE2, HIF1A, ADAMTS5, and BMP2. Increased expression levels of each of these genes correlates positively with a painful intervertebral disc. In other words, an increased expression level of one or more of these genes in a tissue of an intervertebral disc indicates that the intervertebral disc is painful.

As noted above, pain indicator gene expression levels can be detected in the annulus fibrosus of an intervertebral disc. Pain indicator genes that can be detected in the annulus fibrosus include: PGE2, HIF1A, ADAMTS5, and BMP2. Increased expression levels of each of these genes correlates positively with a painful intervertebral disc. In other words, an increased expression level of one or more of these genes in the annulus fibrosus of an intervertebral disc indicates that the intervertebral disc is painful.

Similarly, pain indicator gene expression levels can be detected in the NP of an intervertebral disc. Pain indicator genes that can be detected in the NP of an intervertebral disc include: BMP7, TNF-$\alpha$, and IL1$\beta$. Increased expression levels of each of these genes correlates positively with a painful intervertebral disc. In other words, an increased expression level of one or more of these genes in the NP of an intervertebral disc indicates that the intervertebral disc is painful.

An increased or a decreased expression level is a level that is significantly above a threshold level, or above a normal range. A threshold level can be a level found in a normal intervertebral disc, e.g., an intervertebral disc that is neither painful nor substantially degenerated. A normal range is a range of expression levels found in normal intervertebral discs from a plurality of subjects, where intervertebral discs are neither painful nor substantially degenerated. For example, an increased gene expression level of a pain indicator gene that, when increased, indicates the presence of a painful intervertebral disc, is a level that is at least about 20%, at least about 25%, at least about 50%, at least about 75%, at least about 2-fold, at least about 5-fold, at least about 10-fold, or greater than 10-fold, above a normal range. As another example, a decreased gene expression level of a pain indicator gene that, when decreased, indicates the presence of a painful intervertebral disc, is a level that is at least about 15%, at least about 20%, at least about 25%, at least about 30%, at least about 35%, at least about 40%, at least about 45%, at least about 50%, at least about 60%, at least about 70%, at least about 80%, or at least about 90%, or more, lower than a normal range.

Expression levels of the above-noted pain indicator genes provide an indication as to whether an intervertebral disc is painful, regardless whether the disc is degenerated.

A subject diagnostic method identifies a painful intervertebral disc, where the pain is due to any of a variety of causes, including, e.g., trauma, exertion, strain, etc.

A subject diagnostic method can identify a painful intervertebral disc, where the disc is located between cervical vertebrae (e.g., between C1 and C2; between C2 and C3; between C3 and C4; between C4 and C5; between C5 and C6; or between C6 and C7); between thoracic vertebrae (e.g., between T1 and T2; between T2 and T3; between T3 and T4; between T4 and T5; between T5 and T6; between T6 and T7; between T7 and T8; between T8 and T9; between T9 and T10; between T10 and T11; or between T11 and T12); between lumbar vertebrae (e.g., between L1 and L2; between L2 and L3; between L3 and L4; or between L4 and L5; between C7 and T1; or between T12 and L1.

Nucleotide sequences of the various pain indicator gene products are known in the art, and can be used to design probes and primers. For example, COL2A (type II collagen) nucleotide sequences are found at, e.g., GenBank Accession Nos. NM_001844 and NM_003150, with corresponding amino acid sequences found at GenBank Accession Nos. NP_001835 and NP_149162; COL9A3 (type IX collagen, alpha 3) nucleotide sequences are found at, e.g., GenBank Accession No. NM_001853, with corresponding amino acid sequences found at GenBank Accession No. NP_001844; AGC1 (aggrecan isoform 1) nucleotide sequences are found at, e.g., GenBank Accession No. NM_001135, with corresponding amino acid sequences found at GenBank Accession No. NP_00126; DCN (decorin proteoglycan) nucleotide sequences are found at, e.g., GenBank Accession Nos. NM_001920, NM_133503, NM_133504, NM_133505, NM_133506, NM_133507, with corresponding amino acid sequences found at GenBank Accession Nos. NP_001911, NP_598010, NP_598011, NP_598012, NP_598013, and NP_598014; MMP3 (matrix metalloproteinase 3) nucleotide sequences are found at, e.g., GenBank Accession Nos. NM_002422 and AK313310, with corresponding amino acid sequences found at GenBank Accession Nos. NP_002413 and BAG36115; MMP13 (matrix metalloproteinase 13) nucleotide sequences are found at, e.g., GenBank Accession No.s NM_002427 and BC074808, with corresponding amino acid sequences found at GenBank Accession Nos. NP_002418 and AAH74808; TIMP1 (tissue inhibitor of metalloproteases-1) nucleotide sequences are found at, e.g., GenBank Accession Nos. NM_003254 and AK311937, with corresponding amino acid sequences found at GenBank Accession Nos. NP_003254 and BAG34878; TIMP3 (tissue inhibitor of metalloproteases-3) nucleotide sequences are found at, e.g., GenBank Accession Nos. NM_000362 and CR456593, with corresponding amino acid sequences found at GenBank Accession Nos. NP_000353 and CAG30479; CD44 nucleotide sequences are found at, e.g., GenBank Accession Nos. M59040 and U40373, with corresponding amino acid sequences found at GenBank Accession Nos. AAA51950 and AAA82949; BMP2 (bone morphogenetic protein 2) nucleotide sequences are found at, e.g., GenBank Accession No. NM_001200, with corresponding amino acid sequences found at GenBank Accession Nos. NP_001191; HIF1 (hypoxia-inducible factor-1) nucleotide sequences are found at, e.g., GenBank Accession Nos. AF208487 and U22431, with corresponding amino acid sequences found at GenBank Accession Nos. AAF20149 and AAC50152; IL8 (interleukin-8) nucleotide sequences are found at, e.g., GenBank Accession Nos. BC013615 and M28130, with corresponding amino acid sequences found at GenBank Accession Nos. AAH13615 and AAA59158; IL1R (interleukin-1 receptor) nucleotide sequences are found at, e.g., GenBank Accession Nos. X16896, M27492, and BC067506, with corresponding amino acid sequences found at GenBank Accession Nos. CAA34773, AAA59137, and AAH67506; PLA2 (phospholipase A2) nucleotide sequences are found at, e.g., GenBank Accession Nos. U03090 and U95301, with corresponding amino acid sequences found at GenBank Accession Nos. AAC28886 and AAB64410; MMP9 (matrix metalloproteinase-9) nucleotide sequences are found at, e.g., GenBank Accession No. NM_004994 with corresponding amino acid sequences found at GenBank Accession No. NP_004985; Col1A1 (type I collagen alpha 1) nucleotide sequences are found at, e.g., GenBank Accession Nos. NM_000088, Z74615, and AF017178 with corresponding amino acid sequences found at GenBank Accession Nos. NP_000079, CAA98968, and AAB94054; TSG6 (tumor necrosis factor-alpha-induced protein 6) nucleotide sequences are found at, e.g., GenBank Accession No. BC030205, with corresponding amino acid sequences found at GenBank Accession No. AAH30205; TSG6 sequences are also found at, e.g., Wisniewcki and Vilcek (1992) *J. Cell Biol.* 116:545; and Nentwich et al. (2002) *J. Biol. Chem.* 277:15354.

BMP7 (bone morphogenetic protein-7) nucleotide sequences are found at, e.g., GenBank Accession Nos. NM_001719, AK312419, and BC008584, with corresponding amino acid sequences found at GenBank Accession No. NP_001710, BAG35329, and AAH08584. PGE2 (prostaglandin E synthase 2) nucleotide sequences are found at, e.g., GenBank Accession Nos. BC011613, BC009397, and NM_004878, with corresponding amino acid sequences found at GenBank Accession Nos. AAH11613, AAH09397, and NP_004869. HIF1A (hypoxia-inducible factor-1 alpha) nucleotide sequences are found at, e.g., GenBank Accession Nos. NM_181054, NM_001530, AF207602, and AF208487, with corresponding amino acid sequences found at GenBank Accession Nos. NP_851397, NP_001521, AAF20140, and AAF20149. Sequences of TNF-α (tumor necrosis factor-alpha) are known in the art; see, e.g., Kajihara et al. (1994) *Biosci. Biotehcnol. Biochem.* 58:2266; Marmenout et al. (1985) *Eur. J. Biochem.* 152:515; and Wang et al. (1985) *Science* 228:149; Pennica et al. (1985) *Proc. Natl. Acad. Sci. USA* 82:6060; and GenBank Accession No. P01375. ADAMTS5 (ADAM metallopeptidase with thrombospondin type 1 motif, 5) nucleotide sequences are found at, e.g., GenBank Accession Nos. NM_007038 and BC093777, with corresponding amino acid sequences found at GenBank Accession Nos. NP_008969 and AAH93777. IL1β (interleukin-1 beta) nucleotide sequences are found at, e.g., GenBank Accession Nos. NM_000576 and M15330, with corresponding amino acid sequences found at GenBank Accession Nos. NP_000567 and AAA59135.

Nucleotide sequences of a pain indicator gene include nucleotide sequences having at least about 75%, at least about 80%, at least about 85%, at least about 90%, at least about 95%, at least about 98%, at least about 99%, or 100%, nucleotide sequence identity to any known pain indicator gene, e.g., nucleotide sequences having at least about 75%, at least about 80%, at least about 85%, at least about 90%, at least about 95%, at least about 98%, at least about 99%, or 100%, nucleotide sequence identity to a COL2A gene, a COL9A3 gene, an AGC1 gene, a DCN gene, an MMP3 gene, an MMP13 gene, a TIMP1 gene, a TIMP3 gene, a CD44 gene, a BMP2 gene, an HIF1 gene, an IL8 gene, an IL1R gene, a PLA2 gene, a TSG6 gene, a MMP9 gene, a Col1A1 gene, a Col3 gene, a BMP7 gene, a TNF-α gene, an IL1β gene, a PGE2 gene, an HIF1A gene, or an ADAMTS5 gene. For example, nucleotide sequences of a pain indicator gene include nucleotide sequences having at least about 75%, at least about 80%, at least about 85%, at least about 90%, at least about 95%, at least about 98%, at least about 99%, or 100%, nucleotide sequence identity to a nucleotide sequence set forth in one of the above-mentioned GenBank entries.

Detection Methods

A subject method involves assaying an expression level of a pain indicator gene. Any suitable means of detecting a pain indicator gene product can be used. A nucleic acid pain indicator gene product can be detected using a nucleic acid probe, a pair of nucleic acid primers, or a combination of a nucleic acid probe and a pair of nucleic acid primers. A polypeptide pain indicator gene product can be detecting using a binding element specific for the polypeptide. Suitable specific binding elements include antibodies. The term "antibody" includes an antigen-binding antibody of any isotype; single-chain Fv; Fab; Fab; Fv; F(ab')$_2$; artificial antibodies; chimeric antibodies; synthetic antibodies; and the like. Suitable antibodies will bind with an affinity of at least $10^{-7}$ M or more, e.g., $10^{-8}$ M or more (e.g., $10^{-9}$ M, $10^{-10}$ M, $10^{-11}$ M, etc.).

Suitable imaging methods include, e.g., radiography, magnetic resonance imaging (MRI), positron emission tomography (PET), single photon emission computed tomography (SPECT), computed tomography (CT), fluoroscopy, luminescence, and any combination of the foregoing.

A subject diagnostic method can be carried out on a biopsied tissue in vitro. A subject diagnostic method can be carried out in vivo, e.g., using MRI, PET, SPECT, or CT.

Where a subject diagnostic method is carried out on a biopsied tissue in vitro, the level of a pain indicator gene product can be assayed in cells of the nucleus pulposus, in cells of the annulus fibrosus, or in both cells of the nucleus pulposus and in cells of the annulus fibrosus. Where a subject diagnostic method is carried out on a biopsied tissue in vitro, the level of a nucleic acid gene product and/or the level of a polypeptide gene product can be assayed.

Measuring a Level of a Polypeptide Gene Product

A level of a polypeptide pain indicator gene product can be measured in vitro, e.g., the level of a polypeptide pain indicator gene product can be measured in cells (e.g., whole cells, cell lysates, cell lysates enriched for polypeptides, etc.) obtained from a biopsy sample of an intervertebral disc tissue.

Methods of measuring a level of a polypeptide gene product in vitro are known in the art and include antibody-based methods such as enzyme-linked immunoabsorbent assay (ELISA); radioimmunoassay (RIA); protein blot analysis; immunohistochemical analysis; and the like. Suitable methods also include proteomics methods, such as mass spectral methods, which are known in the art.

In vivo methods of measuring a level of a polypeptide pain indicator gene product can be carried out using a specific binding element (e.g., an antibody) that specifically binds to a polypeptide pain indicator gene product.

For example, a pain indicator gene product can be directly visualized by a specific binding element that comprises a detectable label. The detectable label may be a radioisotope or a fluorochrome that can be visualized by imaging techniques including radiography, MRI, PET, SPECT, CT, or fluoroscopy. For example radioisotope can include $^{18}$F, $^3$H, $^{124}$I, $^{125}$I, $^{131}$I, $^{35}$S, $^{14}$C, and $^{11}$C.

The label may be a radioisotope, such as, for example, $^{18}$F, $^3$H, $^{124}$I, $^{125}$I, $^{131}$I, $^{35}$S, or $^{14}$C. These labels may be attached to a binding element, for example an antibody, by using a chelating agent, such as ethylenediaminetetraacetic acid (EDTA) or diethylenetriaminepentaacetic acid (DTPA), and detected by gamma counter, scintillation counter, PET scanning, or autoradiography.

An antibody that binds specifically to a polypeptide pain indicator gene product can be detectably labeled. Detectable labels include, e.g., radioisotopes (e.g., $^{18}$F, $^3$H, $^{124}$I, $^{125}$I, $^{131}$I, $^{35}$S, $^{14}$C, and $^{11}$C); fluorescent proteins; enzymes that act on a substrate to yield a detectable product, e.g., a colored product, a luminescent product, a fluorescent product, etc., where suitable enzymes include, e.g., β-galactosidase, luciferase, horse radish peroxidase, alkaline phosphatase, etc.; magnetic particles; and the like.

Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; a yellow fluorescent protein; a red fluorescent protein; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

Measuring a Level of a Nucleic Acid Gene Product

In general, methods of measuring a level of a nucleic acid gene product (e.g., an mRNA) include methods involving hybridization analysis of polynucleotides, and methods involving amplification of polynucleotides. In many cases, measuring a level of a nucleic acid gene product is carried out in vitro, e.g., on nucleic acid obtained from cells of a biopsy sample of an intervertebral disc tissue.

Commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes.

Hybridization Methods

Nucleic acid hybridization methods that are suitable for use in a subject method are described below. The level of a target nucleic acid (e.g., a pain indicator nucleic acid) can be measured using a probe that hybridizes to the target nucleic acid. In some embodiments, the target nucleic acid is first amplified, e.g., using a polymerase chain reaction (PCR) method.

A number of methods are available for analyzing nucleic acids for the presence and/or level of a specific nucleic acid. mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), Science 239:487, and a review of techniques may be found in Sambrook, et al. Molecular Cloning: A Laboratory Manual, CSH Press 1989, pp. 14.2-14.33.

In some embodiments, the method involves contacting a sample (e.g., a sample containing nucleus pulposus cells; a sample containing annulus fibrosus cells) under stringent hybridization conditions with a nucleic acid probe and detecting binding, if any, of the probe to a nucleic acid in the sample. A variety of nucleic acid hybridization methods are well known to those skilled in the art, and any known method can be used. In some embodiments, the nucleic acid probe will be detectably labeled.

Amplification Methods

Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.).

A target mRNA can be amplified by reverse transcribing the mRNA into cDNA, and then performing PCR (reverse transcription-PCR or RT-PCR). Alternatively, a single enzyme may be used for both steps as described in U.S. Pat. No. 5,322,770.

The fluorogenic 5' nuclease assay, known as the TAQMAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of a target nucleic acid as described herein can be used in TAQMAN™ analyses to detect a level of target mRNA in a biological sample. Analysis is performed in conjunction with thermal cycling by monitoring the generation of fluorescence signals.

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

The first step is the isolation of mRNA from a target sample. The starting material is typically total RNA isolated from cells of an intervertebral disc. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andrés et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from cells can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

The PCR step can use a variety of thermostable DNA-dependent DNA polymerases; for example, a suitable polymerase is the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In an exemplary embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize the effect of sample-to-sample variation, quantitative RT-PCR can be performed using an internal standard, or one or more reference genes. The ideal internal standard is expressed at a constant level among different tissues, and is unaffected by the experimental treatment. RNAs that can be used to normalize patterns of gene expression include, e.g., mRNAs for the reference genes glyceraldehyde-3-phosphate-dehydrogenase (GAPDH) and β-actin.

A variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a reference gene for RT-PCR. For further details see, e.g. Held et al., *Genome Research* 6:986-994 (1996).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50° C. and 80° C., e.g. about 50° C. to 70° C. can be used.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T.N. Primerselect: Primer and probe design. *Methods Mol. Biol.* 70:520-527 (1997), the entire disclosures of which are hereby expressly incorporated by reference.

Preparing a Report

As described above, a subject method involves diagnosing a painful intervertebral disc. A subject method can further include a step of preparing a report that includes a description of the results of the diagnostic method. For example, a subject method can further include a step of generating or outputting a report providing the results of a subject diagnostic method, which report can be provided in the form of an electronic medium (e.g., an electronic display on a computer monitor), or in the form of a tangible medium (e.g., a report printed on paper or other tangible medium). The report can include, in addition to the results of the diagnostic method, patient information (e.g., age, health status, and the like). The report can include information as to whether an intervertebral disc is painful, and information as to which intervertebral disc is painful.

Treating a Painful Intervertebral Disc

In some embodiments, a subject method involves diagnosing a painful intervertebral disc, as described above; and further involves administering a therapy for treatment of the painful intervertebral disc. Therapy for treatment of a painful intervertebral disc can include one or more of: surgical removal of all or a portion of the painful intervertebral disc; replacement of all or a portion of the painful intervertebral disc; and delivery of a therapeutic agent to a local site to treat the painful intervertebral disc.

Surgical methods include, e.g., surgical removal of all or a portion of a painful intervertebral disc; electrosurgical ablation of painful intervertebral disc tissue (see, e.g., U.S. Pat. No. 7,318,823; and RE40,156). Methods of replacing all or a portion of a painful intervertebral disc are known in the art. For example, all or a portion of a painful intervertebral disc can be replaced with a prosthetic disc or disc tissue (see, e.g., U.S. Pat. Nos. 7,331,994 and 6,187,048).

Therapeutic agents that are suitable for administering in a therapeutic method to treat a painful intervertebral disc include, e.g., collagen; an analgesic; a steroidal anti-inflammatory drug; a non-steroidal anti-inflammatory drug; an anti-TNF-alpha agent; a matrix metalloproteinase inhibitor; and the like. Other agents that can be administered together with an agent that reduces pain include, e.g., an antibiotic; a proteoglycan (e.g., aggrecan); a glycosaminoglycan (e.g., hyaluronic acid; chondroitin sulfate; heparan sulfate); and the like.

Treatment Methods

The present disclosure provides methods of treating a painful intervertebral disc. The methods generally involve administering to an individual having a painful intervertebral disc an effective amount of an agent that increases the level of a tumor necrosis factor-alpha-induced protein 6 (TSG6) polypeptide in a tissue of the painful intervertebral disc. Suitable agents include, e.g., a TSG6 polypeptide; a polynucleotide comprising a nucleotide sequence encoding a TSG6 polypeptide (a "TSG6 polynucleotide"); and a small molecule agent that increases the level of a TSG6 polypeptide in a cell. The terms "active agent" and "drug," are used interchangeably to refer to a TSG6 polypeptide, a TSG6 polynucleotide, and a small molecule agent that increases the level of a TSG6 polypeptide in a cell. In some embodiments, an effective amount of an active agent is an amount that reduces pain in the subject. In other embodiments, an effective amount of an active agent is an amount that results in a level of a pain indicator gene product that is within a normal range.

TSG6 Polypeptides

A TSG6 polypeptide includes a polypeptide comprising an amino acid sequence having at least about 75%, at least about 80%, at least about 85%, at least about 90%, at least about 95%, at least about 98%, at least about 99%, or 100%, amino acid sequence identity to a contiguous stretch of from about 90 amino acids (aa) to about 100 aa, from about 100 aa to about 125 aa, from about 125 aa to about 150 aa, from about 150 aa to about 175 aa, from about 175 aa to about 200 aa, from about 200 aa to about 250 aa, or from about 250 aa to 277 aa, of the amino acid sequence depicted in FIG. 3A (SEQ ID NO:1). For example, a TSG6 polypeptide includes a hyaluronic acid-binding polypeptide having comprising an amino acid sequence having at least about 75%, at least about 80%, at least about 85%, at least about 90%, at least about 95%, at least about 98%, at least about 99%, or 100%, amino acid sequence identity to a contiguous stretch of from about 90 amino acids (aa) to about 100 aa, from about 100 aa to about 125 aa, from about 125 aa to about 150 aa, from about 150 aa to about 175 aa, from about 175 aa to about 200 aa, from about 200 aa to about 250 aa, or from about 250 aa to 277 aa, of the amino acid sequence depicted in FIG. 3A, where the contiguous stretch includes at least amino acids 36-128 of the amino acid sequence depicted in FIG. 3A. Thus, e.g., a TSG6 polypeptide includes a hyaluronic acid-binding polypeptide having comprising an amino acid sequence having at least about 75%, at least about 80%, at least about 85%, at least about 90%, at least about 95%, at least about 98%, at least about 99%, or 100%, amino acid sequence identity to amino acids 36-128 of the amino acid sequence depicted in FIG. 3A, where the TSG6 polypeptide has a length of from about 90 amino acids to about 100 aa, from about 100 aa to about 125 aa, from about 125 aa to about 150 aa, from about 150 aa to about 175 aa, from about 175 aa to about 200 aa, from about 200 aa to about 250 aa, or from about 250 aa to 277 aa.

Formulations suitable for delivery of a polypeptide agent (e.g., a TSG6 polypeptide) to a subject, as well as method of delivery of polypeptide agents, are available in the art. A TSG6 polypeptide can be administered together with a suitable pharmaceutically acceptable carrier or excipient. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration.

In some embodiments, a TSG6 polypeptide composition is formulated in accordance with routine procedures as a pharmaceutical composition adapted for bolus injection or infusion at a local site into an individual. For example, pharmaceutical compositions for injection are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

A TSG6 polypeptide can be delivered by a controlled-release or sustained release system. For example, a TSG6 polypeptide may be administered using intravenous infusion, an implantable osmotic pump, a transdermal patch, liposomes, or other modes of administration. In one embodiment, a pump may be used (See, e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, a TSG6 polypeptide can be delivered in a vesicle, e.g., a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105).

Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(–)-3-hydroxybutyric acid (EP 133,988). Sustained-release TSG6 polypeptide compositions also include liposomally entrapped TSG6 polypeptide. Liposomes containing a TSG6 polypeptide are prepared by methods known per se: DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. The liposomes can be of the small (from or about 200 to 800 Angstroms) unilamellar type in which the lipid content is greater than about 30 mol percent cholesterol, the selected proportion being adjusted for the optimal therapy.

In yet another embodiment, a controlled release system can be placed in proximity (e.g., within about 10 cm, within about 5 cm, or within about 1 cm) of the target (e.g., a painful intervertebral disc). For example, a micropump may deliver controlled doses at or near a painful intervertebral disc, thereby requiring only a fraction of the systemic dose (See, e.g., Goodson, 1984, in *Medical Applications of Controlled Release*, vol. 2, pp. 115-138).

In one embodiment, it may be desirable to administer a TSG6 polypeptide locally to the area in need of treatment; this may be achieved, for example, and not by way of limitation, by local infusion during surgery, bolus injection, by means of a catheter, or by means of an implant (e.g., a pump, a depot, or other implantable device adapted for sustained-release delivery of an agent). An implant can be of a porous, non-porous, or gelatinous material, including membranes, such as sialastic membranes, or fibers.

TSG6 Polynucleotides

A suitable TSG6 polynucleotide comprises an amino acid sequence that encodes a TGS6 polypeptide. A TGS6 polynucleotide includes a polynucleotide comprising an amino acid sequence having at least about 75%, at least about 80%, at least about 85%, at least about 90%, at least about 95%, at least about 98%, at least about 99%, or 100%, nucleotide sequence identity to the nucleotide sequence depicted in FIG. 3B (SEQ ID NO:2).

A TSG6 polynucleotide can be part of an expression vector. The expression vector will provide a transcriptional and translational initiation region, which may be inducible or constitutive, where the coding region is operably linked under the transcriptional control of the transcriptional initiation region, and a transcriptional and translational termination region.

Expression vectors generally have convenient restriction sites located near the promoter sequence to provide for the insertion of nucleic acid sequences encoding heterologous proteins (e.g., a polynucleotide comprising a nucleotide sequence encoding a TSG6 polypeptide). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Non-limiting examples of suitable eukaryotic promoters (promoters functional in a eukaryotic cell) include cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A TSG6 polynucleotide can be delivered in a pharmaceutically acceptable carrier. Pharmaceutically acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated herein by reference. For example, preservatives, stabilizers, dyes and flavoring agents can be provided. These include sodium benzoate, sorbic acid and esters of p-hydroxybenzoic acid. In addition, antioxidants and suspending agents can be used.

Delivery to a local site (e.g., within about 10 cm, within about 5 cm, or within about 1 cm, of a painful intervertebral disc) can be accomplished by, for example, local administration of a nucleic acid agent (e.g., a polynucleotide comprising a nucleotide sequence encoding a TSG6 polypeptide). Conventional approaches that can be used include, but are not limited to, intrathecal administration, intravertebral administration, implantation of catheters and pumps, direct injection or perfusion at or near the painful intervertebral disc, and the like. Other approaches can include the use of various transport and carrier systems, for example though the use of conjugates and biodegradable polymers. See also, U.S. Pat. No. 6,180,613; WO 04/013280, describing delivery of nucleic acid molecules, which are incorporated herein by reference.

Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, nucleic acids can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid is formulated as described in U.S. Patent Application Publication No. 20030077829, incorporated by reference herein in its entirety.

Small Molecule Agents

Small molecule agents that are suitable for use include agents that increase the level of a TSG6 polypeptide in a cell. Small molecule agents include agents having a molecular weight of from about 50 Daltons (Da) to about 20,000 Da, e.g., from about 50 Da to about 100 Da, from about 100 Da to about 500 Da, from about 500 Da to about 1000 Da, from about 1 kDa to about 5 kDa, from about 5 kDa to about 10 kDa, from about 10 kDa to about 15 kDa, or from about 15 kDa to about 20 kDa.

An exemplary small molecule agent is 2-methyoxyestradiol. A small molecule agent can be administered together with a suitable pharmaceutically acceptable carrier or excipient. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A small molecule agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, a subject active agent is delivered by a continuous delivery system. As described in more detail below, a continuous delivery system encompasses continuous (e.g., controlled) delivery devices (e.g., pumps) in combination with catheters, injection devices, and the like, a wide variety of which are known in the art.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Controlled Release Delivery

In some embodiments, an agent (e.g., a TSG6 polypeptide, a TSG6 polynucleotide, a small molecule agent that increases the level of a TSG6 polypeptide in a cell) is delivered by a controlled release ("sustained release") or continuous delivery system. The term "continuous delivery system" is used interchangeably herein with "controlled delivery system," "controlled release system," and "sustained release system," and encompasses continuous (e.g., controlled) delivery devices (e.g., pumps) in combination with catheters, injection devices, and the like, a wide variety of which are known in the art.

Mechanical or electromechanical infusion pumps can also be suitable for use in connection with a subject treatment method. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use in connection with a subject treatment method. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, adjacent or near an intervertebral disc, or other suitable site within a subject's body.

In some embodiments, an active agent is delivered using an implantable drug delivery system, e.g., a system that is programmable to provide for administration of an active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for use in connection with a subject treatment method is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Dosages and Dosing

Depending the agent, an active agent may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Higher doses can be used for localized routes of delivery.

For example, an active agent can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose. An exemplary dosage may be a solution suitable for administration via bolus injection; a solution to be delivered by a controlled-release delivery system; etc.

In some embodiments, multiple doses of an active agent are administered. The frequency of administration of an active agent can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

As noted above, suitable routes of administration include local routes of administration, e.g., administration to a site that is within about 10 cm, within about 5 cm, or within about 1 cm, of a painful intervertebral disc. Suitable routes of administration include, e.g., subcutaneous, intrathecal, intervertebral, and the like.

Subjects Suitable for Diagnosis or Treatment

Subjects suitable for diagnosis with a subject diagnostic method include individuals suffering from back pain. Subjects may or may not have undergone a prior treatment for the back pain.

Subjects suitable for treatment with a subject treatment method include individuals who have been diagnosed with intervertebral disc pain. In some embodiments, the individual is one who has intervertebral disc pain in the absence of rheumatoid arthritis and/or osteoarthritis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Molecular Markers of Painful Intervertebral Discs

Materials and Methods

Disc Specimens

Tissues acquired during lumbar surgery were divided into 3 groups: 1) disc degeneration with pain (disc arthroplasty or fusion); 2) disc degeneration without pain (adult scoliosis); and 3) normal discs (juvenile scoliosis or trauma). Number of patients used per group n=4.

Total RNA Extraction

Disc specimens were collected from the operating room, immediately snap frozen, and stored −70° C. At the time of tissue homogenizing 0.5-1 g of annulus and nucleus were immersed in liquid nitrogen and pulverized with MM301 Retsch ball mill. The homogenization process included 2 cycles of 3 min homogenization at frequency 30/sec.

The resulting sample powder was resuspended in Trizol reagent and RNA was extracted using an Invitrogen column system.

cDNA Amplification and Labeling 50 ng of total RNA were used for first strand cDNA synthesis, followed by second strand cDNA synthesis and cDNA purification (NuGEN technology). 5 µg of amplified cDNA were used for cDNA fragmentation and labeling (NuGEN Technology).

Gene Array and Statistical Analysis

The expression pattern of the disc tissue was analyzed using Human Genome U133A2.0 Gene Array (Affymetrix). Expression levels of thirty-six candidate genes were quantified. In addition, expression levels for the entire Human Genome were evaluated to identify novel markers. Significant differences in expression patterns were determined using LOD scoring and statistical analysis.

Results

Using the candidate gene approach nucleus samples clustered into two groups: the painful disc samples and the non-painful samples (both degenerated and non-degenerated). This trend was not observed in annulus samples.

Nucleus Samples (FIG. 1)

Genes down regulated in painful samples:
1) Several matrix protein genes such as COL2A; COL9A3; AGC1; DCN;
2) MMP3 and MMP13; TIMP1 and TIMP3; CD44;
3) Growth factor BMP2, HIF1;
4) IL8; IL1R; PLA2; TSG6.

Figure 2:
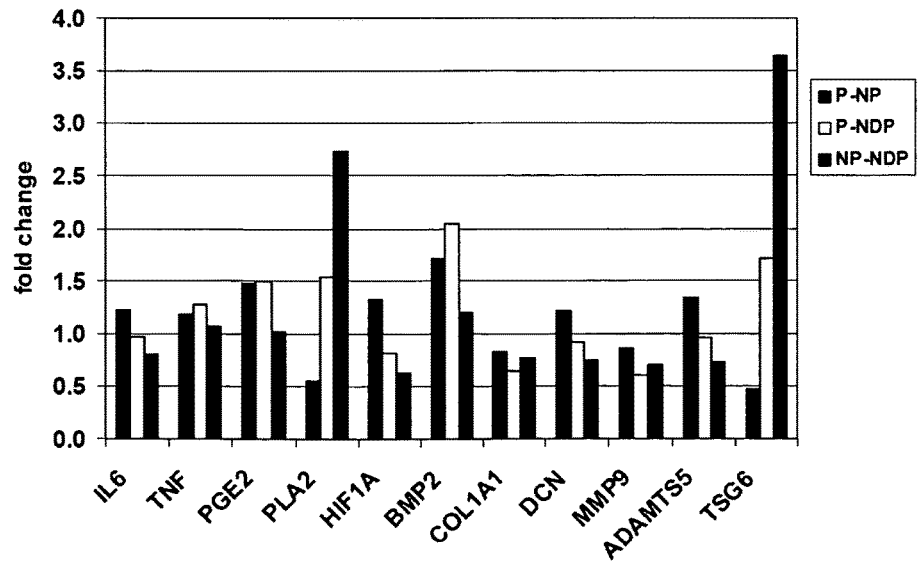
FIG. 2 depicts gene expression of annulus fibrosus samples (P=painful; NP=non painful degenerated; NDP=non painful non degenerated). For each gene, the first bar is P-NP; the second bar is P-NDP; and the third bar is NP-NDP.

Genes up-regulated in painful samples:
1) BMP7; TNF-α; IL1β;

Genes up regulated in degenerated non-painful samples:
1) BMP2; TIMP3; PLA2 (3 fold);
2) TSG6 (7 fold);

Annulus Samples (FIG. 2)

Genes down regulated in painful samples:
1) PLA2; MMP9; TSG6;
2) Col1A1; Col3;

Genes up regulated in painful samples:
1) PGE2; HIF1A; ADAMTS5; BMP2;

Genes up regulated in degenerated non-painful samples:
1) PLA2; BMP2; TSG6 (3 fold).

FIG. 1 depicts gene expression of nucleus pulposus samples (P=painful; NP=non painful degenerated; NDP=non painful non degenerated). FIG. 2 depicts gene expression of annulus fibrosus samples (P=painful; NP=non painful degenerated; NDP=non painful non degenerated).

These data indicate the existence of phenotypic characteristics associated with pain, and that pain is independent of degeneration. Examples include: down regulation of a traditional disc cell marker CD44, and healing dysregulation (e.g. decreased levels of IL8 and TSG6). An important trend has been seen for TSG6 in both annulus and nucleus samples: down regulation of TSG6 was observed in painful samples.

Abbreviations: PLA2: Phospholipase A2; PGE2: Prostaglandin E2; TSG6: Tumor necrosis factor alpha simulated gene-6.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a painful intervertebral disc in an individual, the method comprising:
   a) detecting the painful intervertebral disc, wherein said detecting comprises assaying for an expression level of a gene product of a pain indicator gene, wherein the pain indicator gene is phospholipase A2 (PLA2), wherein a decreased expression level of a PLA2 gene product in an intervertebral disc tissue, compared to a nonpainful degenerated disc reference sample, indicates that the intervertebral disc is painful; and
   b) administering an effective amount of a tumor necrosis factor-alpha induced protein 6 (TSG6) polypeptide, wherein the TSG6 polypeptide comprises an amino acid sequence having at least 95% amino acid sequence identity to the amino acid sequence set forth in SEQ ID NO:1.

2. The method of claim 1, wherein the intervertebral disc tissue is annulus fibrosus.

3. The method of claim 1, wherein the intervertebral disc tissue is nucleus pulposus.

4. The method of claim 1, wherein the gene product is a nucleic acid.

5. The method of claim 1, wherein the gene product is a polypeptide.

6. The method of claim 5, wherein said identifying comprises contacting the intervertebral disc tissue with an antibody specific for the polypeptide.

7. The method of claim 6, wherein the antibody is detectably labeled.

8. The method of claim 7, wherein binding of the detectably labeled antibody to the polypeptide is detected using an imaging method selected from magnetic resonance imaging, positron emission tomography, and single photon emission computed tomography.

9. The method of claim 1, further comprising generating a report comprising information and/or a statement regarding the presence of a painful intervertebral disc in the individual.

10. The method of claim 9, wherein the report is provided in an electronic medium.

11. The method of claim 9, wherein the report is provided in a tangible medium.

12. The method of claim 1, wherein the expression level of the PLA2 gene product in the intervertebral disc tissue is 50% or less compared to the nonpainful degenerated disc sample.

13. The method of claim 1, further comprising diagnosing the painful intervertebral disc when the decreased expression level of the PLA2 gene product in the intervertebral disc tissue, compared to a nonpainful degenerated disc reference sample, is detected.

14. The method of claim 1, further comprising obtaining the intervertebral disc tissue from the individual.

15. A method of detecting phospholipase A2 (PLA2) in a painful intervertebral disc tissue in an individual, the method comprising:

a) obtaining the painful intervertebral disc tissue from the individual;
b) assaying for an expression level of PLA2;
c) detecting whether PLA2 is present in the painful intervertebral disc tissue at an expression level that is lower than the level of PLA2 in a nonpainful degenerated disc reference sample; and
d) outputting a report on said detecting step.

16. The method of claim 15, wherein the intervertebral disc tissue is annulus fibrosus.

17. The method of claim 15, wherein the intervertebral disc tissue is nucleus pulposus.

18. The method of claim 15, further comprising diagnosing the painful intervertebral disc when the decreased expression level of the PLA2 gene product in the intervertebral disc tissue, compared to a nonpainful degenerated disc reference sample, is detected.

* * * * *

SEQUENCE LISTING

```
<160> NUMBER OF SEQ ID NOS: 2

<210> SEQ ID NO 1
<211> LENGTH: 277
<212> TYPE: PRT
<213> ORGANISM: Homo sapiens

<400> SEQUENCE: 1

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190
```

```
Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
                260                 265                 270

Arg Phe Ser His Leu
        275

<210> SEQ ID NO 2
<211> LENGTH: 834
<212> TYPE: DNA
<213> ORGANISM: Homo sapiens

<400> SEQUENCE: 2
atgatcatct taatttactt atttctcttg ctatgggaag acactcaagg atggggattc      60
aaggatggaa tttttcataa ctccatatgg cttgaacgag cagccggtgt gtaccacaga    120
gaagcacggt ctggcaaata caagctcacc tacgcagaag ctaaggcggt gtgtgaattt    180
gaaggcggcc atctcgcaac ttacaagcag ctagaggcag ccagaaaaat tggatttcat    240
gtctgtgctg ctggatggat ggctaagggc agagttggat accccattgt gaagccaggg    300
cccaactgtg gatttggaaa aactggcatt attgattatg gaatccgtct caataggagt    360
gaaagatggg atgcctattg ctacaaccca cacgcaaagg agtgtggtgg cgtctttaca    420
gatccaaagc aaattttaa atctccaggc ttcccaaatg agtacgaaga taaccaaatc    480
tgctactggc acattagact caagtatggt cagcgtattc acctgagttt tttagatttt    540
gaccttgaag atgacccagg ttgcttggct gattatgttg aaatatatga cagttacgat    600
gatgtccatg gctttgtggg aagatactgt ggagatgagc ttccagatga catcatcagt    660
acaggaaatg tcatgacctt gaagtttcta agtgatgctt cagtgacagc tggaggtttc    720
caaatcaaat atgttgcaat ggatcctgta tccaaatcca gtcaaggaaa aaatacaagt    780
actacttcta ctggaaataa aaactttta gctggaagat ttagccactt ataa          834
```